US010300134B1

(12) United States Patent
Briell et al.

(10) Patent No.: US 10,300,134 B1
(45) Date of Patent: May 28, 2019

(54) VACCINE FORMULATIONS AND METHODS OF PREPARATION AND USE THEREOF

(71) Applicant: Tejas Discovery and Research, LLC, Seguin, TX (US)

(72) Inventors: Claudia Briell, Seguin, TX (US); William C. Campaigne, Seguin, TX (US); Jeff Nelson, Seguin, TX (US)

(73) Assignee: Tejas Discovery and Research, LLC, Seguin, TX (US)

( * ) Notice: Subject to any disclaimer, the term of this patent is extended or adjusted under 35 U.S.C. 154(b) by 0 days.

(21) Appl. No.: 15/349,196

(22) Filed: Nov. 11, 2016

Related U.S. Application Data

(60) Provisional application No. 62/253,991, filed on Nov. 11, 2015.

(51) Int. Cl.
*A61K 39/38* (2006.01)
*A61K 9/19* (2006.01)
*A61K 39/00* (2006.01)
*A61K 9/16* (2006.01)

(52) U.S. Cl.
CPC ............ *A61K 39/38* (2013.01); *A61K 9/1652* (2013.01); *A61K 9/1682* (2013.01); *A61K 2039/54* (2013.01); *A61K 2039/552* (2013.01)

(58) Field of Classification Search
None
See application file for complete search history.

(56) References Cited

U.S. PATENT DOCUMENTS

2012/0231044 A1* 9/2012 Herst .................... A61K 9/145
424/400

OTHER PUBLICATIONS

Wallis et al., Western Veterinary Conference, pp. 1-5. (Year: 2005).*
Ahire et al, Drug Devleopment and Industrial Pharmacy, 33, pp. 1112-1124. (Year: 2007).*
Mohammadpour Dounighi et al., The Journal of Venomous Animals and Toxins including Tropical Diseases, 18(1), pp. 44-52. (Year: 2012).*
Mohammadpour Dounighi et al., Nanomedicine: Nanotechnology, Biology, and Medicine, 6, pp. 137-143. (Year: 2010).*
Li et al., Clinical and Developmental Immunology, pp. 1-8. (Year: 2013).*
Scherlie, Regina, et al., "In vivo evaluation of chitosan as an adjuvant in subcutaneous vaccine formulations"; Vaccine, vol. 31, 2013, Elsevier Ltd.; pp. 4812-4819.
M. J. Leonard et al., "Effects of the canine rattlesnake vaccine in moderate to severe cases of canine crotalid envenomation", Dovepress, Veterinary Medicine: Research and Reports 2014:5 153-158 (6 pages).
Leerburg; Leerburg Q&A; "Our dog had a reaction to the rattlesnake vaccine, which according to our vet is unusual. What do you think!"; http://leerburg.com/qa/qna.php?id=2063; retrieved Dec. 26, 2017 (5 pages).
"Terrierman's Daily Dose: Snake Bit at the Veterinarians Office?"; Jul. 9, 2015; https://terriermandotcom.blogspot.com/2015/07/snake-bit-at-veterinarians-office.html; retrieved Dec. 26, 2017 (8 pages).
Leerburg; Leerburg Webboard: Rattlesnake vaccine; http://leerburg.com/webboard/thread.php?topic_id=18408&page=2; retrieved Dec. 26, 2017 (6 pages).
"Terrierman's Daily Dose: Snake Oil or Snake Vaccine?"; Jun. 11, 2010; https://terriermandotcom.blogspot.com/2010/06/snake-oil-or-snake-vaccine.html; retrieved Dec. 26, 2017 (8 pages).
Dr. Jeennie Thomason; "Rattlesnake Vaccine for My Dogs? No Thanks!"; American Council of Animal Naturopathy; Apr. 22, 2015; https://www.animalnaturopathy.org/rattlesnake-vaccine-for-my-dogs-no-thanks/; retrieved Dec. 26, 2017 (9 pages).
How Does the Rattlesnake Vaccine Work?; The Pets Most Likely to Suffer from Vaccine Adverse Reactions; https://healthypets.mercola.com/sites/healthypets/archive/2013/11/08/rattlesnake-vaccine.aspx; retrieved Dec. 26, 2017 (9 pages).
Dr. Jennifer Coates; The Daily Vet; Canine Vaccination Series: Part 2—Rattlesnake Vaccinations for Dogs | petMD; https://www.petmd.com/blogs/fullyvetted/2013/july/canine-vaccination-series part 2 rattlesnake-vaccines-30527#; retrieved Dec. 26, 2017 (3 pages).
L. V. Welborn et al.; "2011 AAHA Canine Vaccination Guidelines"; Veterinary Practice Guidelines; American Animal Hospital Association, Sep./Oct. 2011 (42 pages).
UC Davis Veterinary Medicine; Canine and Feline Vaccination Guidelines | UC Davis School of Veterinary Medicine—Veterinary Medical Teaching Hospital; http://www.vetmed.ucdavis.edu/vmth/small_animal/internal_medicine/newsletters/vaccination_protocols.cfm; retrieved Dec. 26, 2017 (6 pages).
C. C. Cates et al.; "Comparison of the protective effect of a commercially available western diamondback rattlesnake toxoid vaccine for dogs against envenomation of mice with western diamondback rattlesnake (*Crotalus atrox*), northern Pacific rattlesnake (*Crotalus oreganus oreganus*), and southern Pacific rattlesnake (*Crotalus oreganus helleri*) venom"; AJVR; vol. 76; No. 3; Mar. 2015; pp. 272-279 (8 pages).
UC Davis Veterinary Medicine; Avoid Snakebite during Summer Pet Outings; http://www.vetmed.ucdavis.edu/whatsnew/article.cfm?id=1883; retrieved Dec. 26, 2017 (1 page).
Adverse Vaccine Reactions; https://acerlux.com/vaccines/vaccinereactions.html; retrieved Dec. 26, 2017 (2 pages).
Letter from Jim Brockett and James McCabe (co-author of Cates et al.) to California Fish and Game Commission, Jan. 30, 2015 (4 pages).

* cited by examiner

*Primary Examiner* — Abigail Vanhorn
(74) *Attorney, Agent, or Firm* — Osha Liang LLP

(57) ABSTRACT

A veterinary vaccine composition may include a pharmaceutically acceptable carrier, a biocompatible polymer; and inactive rattlesnake venom. Embodiments may also relate to methods of triggering an immune response in an animal by administering a vaccine composition (containing inactive rattlesnake venom) to the animal and/or methods of formulating a vaccine composition.

15 Claims, No Drawings

VACCINE FORMULATIONS AND METHODS OF PREPARATION AND USE THEREOF

CROSS-REFERENCE TO RELATED APPLICATIONS

This application claims priority to U.S. Patent Application No. 62/253,991, filed on Nov. 11, 2015, which is herein incorporated by reference in its entirety.

BACKGROUND

Technical Field

Embodiments disclosed herein relate generally to vaccines and methods relating thereto.

Background Art

While the number of humans bitten by a rattlesnake in the United State is around seven to eight thousand per year (according to the Center for Disease Control), the number of domesticated animals bitten per year in the United States is estimated to be at least 150,000 and potentially as much as 300,000. For example, dogs are estimated to be about 20 times more likely to be bitten by venomous snakes than humans and are about 25 times more likely than humans to die if bitten.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a veterinary vaccine composition that includes a pharmaceutically acceptable carrier, a biocompatible polymer; and inactive rattlesnake venom.

In another aspect, embodiments disclosed herein relate to a method of triggering an immune response in an animal that includes administering a vaccine composition to the animal, the vaccine composition comprising inactive rattlesnake venom, a biocompatible polymer, and a pharmaceutically acceptable carrier.

In yet another aspect, embodiments disclosed herein relate to a method of formulating a vaccine composition that includes rehydrating a mixture of lyophilized antigen, linear chitosan, and a crosslinking agent, and crosslinking the chitosan upon rehydration.

In yet another aspect, embodiments disclosed herein relate to a method of formulating a vaccine composition that includes inactivating a rattlesnake venom; adding a crosslinking agent to the inactivated rattlesnake venom; adding the combined inactivated rattlesnake venom and crosslinking agent to a solution containing a polymeric carrier.

In yet another aspect, embodiments disclosed herein relate to a composition that includes a pharmaceutically acceptable carrier, a plurality of microspheres formed from crosslinked chitosan, and an antigen carried in the plurality of microspheres.

Other aspects and advantages of the claimed subject matter will be apparent from the following description and the appended claims.

DETAILED DESCRIPTION

In one aspect, embodiments disclosed herein relate to vaccines, including methods of preparation and use thereof. Specifically, one or more embodiments of the present disclosure may relate to *Crotalus atrox* toxoid vaccines that may include an amount of inactive rattlesnake venom present in a veterinary vaccine. Upon administration of the vaccine, an antibody response may be induced in the vaccinated animal, such as dogs, horses, and cats. One or more embodiments also relate to the use of chitosan microspheres as a carrier for antigens.

In one or more embodiments, the vaccine of the present disclosure may be a toxoid vaccine, i.e., containing inactive toxin, such as rattlesnake venom. Such venom may be from, for example, *Crotalus atrox*, i.e., the Western Diamondback Rattlesnake. The venom or toxins may be inactivated by one or more of any means, such as chemical, thermal, electromagnetic radiation treatments such that it may induce an immunological response in the animal without or with reduced toxicity to the animal. Upon inactivation, the inactive venom or toxin may also be referred to as a toxoid. In one or more embodiments, the toxicity of the venom may be suppressed by exposure to temperatures of at least 75° C., 80° C., or 90° C., such as for a period of time of at least 2 minutes, 3 minutes, 4 minutes, or 5 minutes. However, depending on the exposure temperature, the amount of time may vary. Further, it is also envisioned that the thermal exposure may be conducted in the presence of one or more chemical treatments, including low pH, exposure to formalin, formaldehyde, paraformaldehyde, β-propiolactone, ethyleneimine, binary ethyleneimine (BEI), thimerosal, or derivatives thereof.

In an embodiment, the composition comprises an amount of toxoid sufficient to cause or stimulate an immune response against the toxin (venom) in treated animals. The exact amount required for an immunologically effective dose may vary from subject to subject depending on factors such as the age, weight, and general condition of the subject, the nature of the formulation and the mode of administration. Appropriate "effective amount" may be determined by one of ordinary skill in the art using only routine experimentation. For instance, methods are known in the art for determining or titrating suitable dosages of vaccine to find minimal effective dosages based on the weight of the non human animal subject, concentration of the vaccine and other typical factors. The dosage of the vaccine, concentration of components therein and timing of administering the vaccine, which elicit a suitable immune response, can be determined by methods such as by antibody titrations of serum, such as by ELISA and/or seroneutralization assay analysis and/or by vaccination challenge evaluation. For example, in one or more embodiments, the concentration of toxoid in the vaccine composition may range from about 1 to 10 mg/mL or from 3 to 7 mg/mL in more particular embodiments, with a dosage ranging from about 1 to 10 mg/dose or from 3 to 7 mg/dose in more particular embodiments.

The antigen (such as toxoid) may be delivered in a polymeric carrier, such as a microsphere. In one or more embodiments, such polymeric carrier may be a biocompatible polymer, such as, for example, chitosan, a cationic polymer that results from the deacetylation of chitin (a polysaccharide found in crustaceans, insects, and lower plants). In one or more embodiments, the degree of deacetylation may be at least about 60, 70, or 75% and up to about 85 or 90%. However, in one or more other embodiments, other biocompatible polymers may be used such as other polysaccharides such as lectins, or other glycosaminoglycans; celluoses; hydroxyaliphatic carboxylic acids, either homo- or copolymers, such as poly(lactic acid), poly(glycolic acid), poly(dl-lactide/glycolide, poly(ethylene glycol); acrylate polymers, and the like. Such biocompatible polymers may optionally take the form of a microsphere and act as a carrier for the inactive venom. The average molecular weight ($M_n$) of the polymeric carrier may range from about 2000 to 20000 Daltons or from 3000 to 8000 Daltons in a more particular embodiment. Further, in some embodiments, the polymer may be crosslinked. For example, in a particular embodiment, chitosan may be used as the polymeric carrier and may be crosslinked with tripolyphosphate. However, it is also envisioned that other crosslinkers, such as glutaraldehyde or epichlorhydrin, may also be used. The ratio between the chitosan and crosslinker may range from 3:1 to 7:1. Further, it is also envisioned that the crosslinked chitosan carrier of the present disclosure may serve as a carrier for other antigens, including but not limited to other toxoids (other than inactive rattlesnake venom).

Microspheres for use in the present disclosure may have any shape, with microspheres which are substantially spherical in shape being preferred. Microspheres for use in the present disclosure may have diameters ranging between about 10 μm to about 2000 μm. Preferably, microspheres for use in the present disclosure will have diameters ranging between 40 pun and 1000 pun. The microspheres of the present disclosure are preferably capable of being injected through needles of 18 gauge or smaller. In such cases, the preferred average diameters of the microspheres are from about 40 μm to about 400 μm and, more preferably, from about 50 to about 200 μm. In a most preferred embodiment, the average diameters of the injectable microspheres range from about 70 to about 120 μm. The microspheres of the present disclosure may be created by rehydration of a lyophilized mixture of the antigen (toxoid), chitosan, and crosslinking agent, or by rehydration of separately lyophilized components that are combined during reconstitution. The inventors of the present disclosure found that encapsulation followed by lyophilization results in a lyophilized encapsulant that is not soluble. Thus, the encapsulation may occur by crosslinking of the polymeric carrier in the presence of the toxoid or other antigen after lyophilization, rather than before lyophilization. The microspheres may be created upon rehydration and used immediately. As mentioned, such polymeric carrier may be used with other toxoids or other antigens, and it is envisioned that the applicability extends beyond veterinary vaccines.

The toxoid may be formulated with a pharmaceutically acceptable carrier or diluent to form a vaccine composition The type of carrier used will depend on the mode of administration of the vaccine including parenteral (including subcutaneous, intramuscular, intravenous and intradermal), oral, implant, rectal, inhalation or insufflation (through the mouth or nose), or topical (including buccal and sublingual) administration. In one or more embodiments, the mode of administration is parenteral and the carrier may be a physiologically acceptable solvent such as physiological saline, aqueous buffer solutions, solvents and/or dispersion media.

Examples of pharmaceutically acceptable carriers, excipients or diluents include, but are not limited to demineralised or distilled water; saline solution; buffer solutions such as acetate buffers; volatile silicones; squalane; cellulose derivatives such as methyl cellulose, ethyl cellulose, carboxymethylcellulose, carboxymethylcellulose sodium salt, or hydroxypropyl methylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar, carrageenan; gum tragacanth or gum acacia, and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like. In one or more embodiments, the carrier may be an immunologically inert chemical substance, such as a buffer and/or a (e.g. buffered) solution of an inorganic salt in water. The carrier may be used to dilute the mixture of the toxoid and the polymeric carrier up to an appropriate concentration.

Preferably, the solution is stable under the conditions of manufacture and storage and preserved against the contaminating action of microorganisms such as bacteria and fungi through the use of for example, parabens, chlorobutanol, phenol, ascorbic acid, thimerosal, and the like.

It is also envisioned that one or more adjuvants (in addition to the polymeric carrier which may act as an adjuvant) may also be included in the vaccine composition. Such adjuvants may include aluminum salts (such as aluminum hydroxide and aluminum phosphate), oil emulsions, such as squalene-containing emulsions, saponins, liposomes, nonionic block copolymers, cytokines, etc. Further, freeze drying stabilizers, wetting or emulsifying agents, pH buffering agents, gelling or viscosity enhancing additives, and preservatives may also be included, depending on the route of administration.

In one or more embodiments, the present disclosure also relates to the methods of making the compositions described above. Specifically, such methods may include the inactivation of rattlesnake venom or other toxins, such as by heat, chemical or physical denaturation, or combinations thereof, as well as the encapsulation of the inactive venom by a polymeric carrier. Optionally, upon inactivation, the toxoid (or other antigen) may be lyophilized and subsequently reconstituted in the vaccine composition. In one or more embodiments, the encapsulation may occur by crosslinking of the polymeric carrier in the presence of the inactive venom. In particular embodiments, the crosslinking agent may be added to the inactive venom prior to lyophilization, the result of which is then reconstituted or combined with the polymeric carrier in a diluent (which may optionally be autoclaved prior to combination with the inactive venom). Subsequent to the above-described two preparation steps of the vaccine composition, the final vaccine composition may also include one or more of the following steps: admixing of an adjuvant or other additives either separately or in parallel; admixing of the pharmaceutically acceptable carrier; and by final steps the product is bottled.

The final packaging steps allow the preparation of, for example, 1 ml doses, which are then ready for the immunization of an animal. Larger volume doses are also possible, for example, for the use in an apparatus designed for the immunization of several animals, one after another in an immunization campaign (e.g. the use of a liquid, jet, needle-free injector).

The vaccine composition according to the disclosure can be administered to the animal to be vaccinated by any appropriate route known to a person skilled in the art. The vaccine composition provided herewith may be administered intradermally, intratracheally, orally, intranasally, intravaginally or intramuscularly. The composition is preferably administered subcutaneously. The vaccines of the disclosure can be administered as single dose or in repeated doses. Vaccines compositions according to the present disclosure may be administered alone, or can be co-administered or sequentially administered with other treatments or therapies. Where the compositions are administered at different times the administrations may be separate from one another or overlapping in time. Typically, the vaccine is administered in the form of dosages of between 0.5 to 3 ml each.

In a preferred embodiment, a vaccine composition according to the present disclosure elicits effective immunity beginning from 3 weeks after immunization (OoI; onset of immunity) and lasts at least for 52 weeks after immunization (DoI; duration of immunity). Increasingly more preferred are earlier onset data of about 2.5 or 2 weeks of OoI, or even earlier, on one side, and longer lasting protection data of about 56, 60, 64 weeks DoI or even longer, on the other side.

The present disclosure provides a container comprising an immunologically effective amount the vaccine as described above. The disclosure also provides vaccination kits comprising an optionally sterile container comprising an immunologically effective amount of the vaccine, means for administering the vaccine to animals, and eventually an instruction manual including information for the administration of the immunologically effective amount the composition into animals for treating rattlesnake bites.

Upon vaccination by the present vaccine composition, a vaccinated animal that is subsequently exposed to rattlesnake venom (or other toxins or antigens, in the case of vaccines for other purposes), including but not limited to a *Crotalus atrox* or other members of the *Crotalus* genus, may present with a reduction of clinical signs conventionally associated with exposure to rattlesnake venom, including swelling, difficulty breathing, low blood pressure, rapid heat rate, ecchymosis, necrosis, uncontrolled bleeding, paralysis, etc. Accordingly, the term "reduction of clinical signs" as reached by the discussed invention, means, but is not limited to, the reduction in severity or incidence of one or more of the signs selected from the group consisting of: swelling, difficulty breathing, low blood pressure, rapid heat rate, ecchymosis, necrosis, uncontrolled bleeding, paralysis. Efficacy of the vaccine may be determined through lab serum neutralization techniques, such as ELISA, whereby certain levels of antibody can determined to neutralize certain levels of toxin.

EXAMPLES

Example 1

Chitosan microspheres were evaluated as a potential carrier for inactivated rattlesnake venom. Low to medium molecular weight chitosan was made into spheres using TPP and was tested at varying concentrations. A microscope was used to detect TPP/chitosan spheres. The tests determined that the best concentrations for chitosan spheres are a chitosan to TPP ratio of 5:1 in acetate buffer.

Example 2

To prepare the venom for inactivation, the venom (20 mg) was added to a phosphate buffered saline (PBS) (10 mL, 10 mM, pH 7.20, sterile filtered). The venom solution was then placed into a 95° C. water bath. The temperature of the solution was monitored and once the solution reached 85° C. a timer was started for five minutes. For the five minute interval the venom solution temperature was kept between 85° C. and 92° C. Next, the venom solution was allowed to cool in a freezer for 15 minutes, and then the volume was adjusted back to 10 mL with sterile filtered PBS. TPP (2 mg/mL) was added to the venom solution. Five 2 mL aliquots of the inactivated venom solution were then placed into five separate 25 mL vials. The vials were then lyophilized for 36 hours.

Next, medium molecular weight chitosan (40 mg) was prepared in an acetate buffer (40 mL, 10 mM, pH 4.6). The chitosan/acetate buffer mixture was placed on a hotplate stirrer and heated to 37° C. while stirred with a magnetic stir bar. The mixture was heated and stirred until the chitosan dissolved into solution. The chitosan solution then was incubated at 37° C. overnight. Next, the chitosan solution was divided into 20 mL aliquots and placed into two separate 50 mL vials. The vials were then autoclaved for 15 minutes at 121° C. The heat of the autoclave step dissolved any chitosan that remained out of solution. The vials were then sealed and capped to keep sterile. The autoclaved chitosan solution was used to reconstitute and act as a time-released carrier for the lyophilized and inactivated venom. Crosslinking of the chitosan may occur after reconstitution of the inactive venom (via the TPP provided with the inactive venom).

A trial of the rattlesnake vaccine in dogs was performed. Five dogs were selected and bled before being vaccinated to get a baseline titer of rattlesnake antibodies. All dogs showed a small initial antibody presence. The most dilute positive titer was 1:200 (seen in dogs number one and four). The five dogs were then injected subcutaneously with the complete vaccine (1 mL, 5 mg/mL), but is believed that dog number two did not receive the complete vaccine. The dogs were then bled every two weeks to determine antibody titers. On week two and week four, elevated antibody titers were found in all dogs. At week four, all of the dogs' antibody titers were up to 1:5120 except for dog two, which was 1:1280, further indicating that dog two did not receive the entire complete vaccine dose. After the week four bleed, each dog received a booster of the complete vaccine (1 mL, 5 mg/mL) subcutaneously. No discomfort or other side effects were been observed. The results are shown in Table 1 below.

TABLE 1

| ID | Titer | Pre | week 4 | week 6 | week 8 | week 10 | week 12 | week 14 |
|---|---|---|---|---|---|---|---|---|
| 1 | 640 | NEG | POS | POS | POS | POS | POS | POS |
|  | 1280 | NEG | POS | POS | POS | POS | POS | POS |
|  | 2560 | NEG | POS | POS | POS | POS | POS | POS |
|  | 5120 | NEG | POS | POS | POS | POS | POS | NEG |
|  | 10240 | NEG | NEG | POS | POS | POS | POS | NEG |
|  | 20480 | NEG | NEG | NEG | NEG | POS | POS | NEG |
|  | 40960 | NEG | NEG | NEG | NEG | POS | NEG | NEG |
|  | 81920 | NEG | NEG | NEG | NEG | NEG | NEG | NEG |
| 2 | 640 | NEG | POS | POS | POS | NOT TESTED | | |
|  | 1280 | NEG | POS | POS | POS | | | |
|  | 2560 | NEG | NEG | POS | POS | | | |
|  | 5120 | NEG | NEG | POS | POS | | | |
|  | 10240 | NEG | NEG | POS | POS | | | |
|  | 20480 | NEG | NEG | NEG | NEG | | | |
|  | 40960 | NEG | NEG | NEG | NEG | | | |
|  | 81920 | NEG | NEG | NEG | NEG | | | |
| 3 | 640 | NEG | POS | POS | POS | POS | POS | POS |
|  | 1280 | NEG | POS | POS | POS | POS | POS | POS |
|  | 2560 | NEG | POS | POS | POS | POS | POS | POS |

TABLE 1-continued

| ID | Titer | Pre | week 4 | week 6 | week 8 | week 10 | week 12 | week 14 |
|---|---|---|---|---|---|---|---|---|
| | 5120 | NEG | POS | POS | POS | POS | POS | POS |
| | 10240 | NEG | NEG | POS | POS | POS | POS | NEG |
| | 20480 | NEG | NEG | POS | POS | POS | POS | NEG |
| | 40960 | NEG | NEG | NEG | NEG | POS | NEG | NEG |
| | 81920 | NEG | NEG | NEG | NEG | POS | NEG | NEG |
| 4 | 640 | NEG | POS | POS | POS | POS | POS | POS |
| | 1280 | NEG | POS | POS | POS | POS | POS | POS |
| | 2560 | NEG | POS | POS | POS | POS | POS | NEG |
| | 5120 | NEG | POS | POS | POS | POS | POS | NEG |
| | 10240 | NEG | NEG | POS | POS | POS | POS | NEG |
| | 20480 | NEG | NEG | NEG | NEG | POS | NEG | NEG |
| | 40960 | NEG | NEG | NEG | NEG | NEG | NEG | NEG |
| | 81920 | NEG | NEG | NEG | NEG | NEG | NEG | NEG |
| 5 | 640 | NEG | POS | POS | POS | POS | POS | POS |
| | 1280 | NEG | POS | POS | POS | POS | POS | POS |

TABLE 1-continued

| ID | Titer | Pre | week 4 | week 6 | week 8 | week 10 | week 12 | week 14 |
|---|---|---|---|---|---|---|---|---|
| | 2560 | NEG | POS | POS | POS | POS | POS | POS |
| | 5120 | NEG | POS | POS | POS | POS | POS | POS |
| | 10240 | NEG | NEG | POS | POS | POS | POS | NEG |
| | 20480 | NEG | NEG | POS | POS | POS | POS | NEG |
| | 40960 | NEG | NEG | NEG | NEG | POS | POS | NEG |
| | 81920 | NEG | NEG | NEG | NEG | POS | NEG | NEG |

Example 2

In this example, a population of rats is injected with one of two vaccines (either the vaccine of the present disclosure or a commercially available vaccine) to determine the efficacy of one versus the other. Weekly tail bleeds and subsequent ELISAs are used to determine titer values for individual rats and averaged to estimate a population. The vaccine of the present disclosure is delivered as 5 mg/mL vials accompanied by a Chitosan Adjuvant (1 mL added) to serve as study group A. A commercially available vaccine from Red Rock Biologicals is delivered as a liquid stating one dose per cc to serve as study group B. Previously a BCA protein determination revealed a protein concentration of ~3 mg/mL for the Red Rock vaccine. Rats are injected subcutaneously with an appropriate volume to deliver 1 mg of vaccine protein per test subject. Booster inoculations are to follow at ~28 days post injection. Tail bleeds will contain at least 1 mL of blood to allow for ~500 μL of plasma for titer determinations. Injection site monitoring included determining any possible injection site maladies or reactions.

Pre-injection titers demonstrated a zero titer for all rats prior to injection. Three week titers at day 21 demonstrated a zero titer for vaccinated rats in study group B and 1:6400 titer for vaccinated rats in study group A. On day 28, each study group received a booster injection of its respective vaccine to deliver 1 mg of vaccine protein per test subject. On day 50, each population was tail bled to determine an average titer for the population. Study group A had an average titer of greater than 1:25600, and study group B had an average titer of 1:280.

On day 51, the populations of rats from study groups A and B, with two negative control subjects, were injected subcutaneously with an $LD_{50}$ (18.5 mg/kg) of C. atrox venom that was rehydrated with 0.9% saline and sterile filtered. The rats were monitored for no less than 2 days to determine the effects of the challenge. The results are shown below in Table 2.

TABLE 2

| Study Group | Rat Number | Rat Weight | LD50 (SC) @ 18.5 mg/kg | Injection @ 20 mg/mL | Challenge Results |
|---|---|---|---|---|---|
| A | 1 | 430 g | 7.955 mg | 0.400 mL | Survived |
| A | 2 | 453 g | 8.381 mg | 0.419 mL | Died day 53 |
| A | 3 | 477 g | 8.825 mg | 0.441 mL | Survived |
| A | 4 | 496 g | 9.176 mg | 0.459 mL | Survived |
| A | 5 | 425 g | 7.863 mg | 0.393 mL | Died day 54 |
| B | 1 | 490 g | 9.065 mg | 0.453 mL | Survived |
| B | 2 | 470 g | 8.695 mg | 0.435 mL | Died day 53 |
| B | 3 | 440 g | 8.140 mg | 0.407 mL | Died day 53 |
| B | 4 | 443 g | 8.200 mg | 0.410 mL | Survived |
| B | 5 | 410 g | 7.585 mg | 0.380 mL | Survived |
| Neg. Control | 1 | 492 g | 9.102 mg | 0.455 mL | Died day 53 |
| Neg. Control | 2 | 455 g | 8.418 mg | 0.421 mL | Survived |

Because it was considered that the filtration in the challenge injection may have removed some of the toxic properties of the venom, each of the surviving rats were subject to a second challenge injection on Day 94 with 15 mg of non-filtered venom per rat given subcutaneously. Titers were also taken. The results of the second challenge injection are shown in Table 3.

TABLE 3

| Study Group | Rat | Titer | Challenge Results |
|---|---|---|---|
| B | 1 | 1:800 | Died day 95 |
| B | 4 | 1:6400 | Died day 95 |
| B | 5 | 1:800 | Died day 95 |
| A | 1 | >1:25600 | Survived |
| A | 3 | >1:25600 | Survived |
| A | 4 | >1:25600 | Survived |
| Neg. Control | 2 | zero | Died day 94 |

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A veterinary vaccine composition, comprising:
a pharmaceutically acceptable carrier,
a biocompatible polymer comprising chitosan; and
a thermally inactivated rattlesnake venom, wherein the thermally inactivated rattlesnake venom is present in in the composition at a concentration ranging from about 1 to 10 mg/mL.

2. The veterinary vaccine composition of claim 1, wherein the biocompatible polymer comprises a plurality of microspheres.

3. The veterinary vaccine composition of claim 2, wherein the inactive rattlesnake venom is encapsulated in the plurality of microspheres.

4. The veterinary vaccine composition of claim 1, wherein the inactive rattlesnake venom is inactive *Crotalus atrox*.

5. The veterinary vaccine composition of claim 1, wherein the pharmaceutically acceptable carrier comprises a buffered solution of an inorganic salt in water.

6. The veterinary vaccine composition of claim 1, wherein the chitosan is crosslinked by tripolyphosphate.

7. The veterinary vaccine composition of claim 6, wherein the ratio between the chitosan and the tripolyphosphate ranges from 3:1 to 7:1.

8. A method of triggering an immune response in an animal, comprising:
administering a vaccine composition to the animal, the vaccine composition comprising a thermally inactivated rattlesnake venom, a biocompatible polymer comprising chitosan, and a pharmaceutically acceptable carrier, wherein the thermally inactivated rattlesnake venom is present in in the composition at a concentration ranging from about 1 to 10 mg/mL.

9. The method of claim 8, further comprising:
administering a booster of the vaccine composition to the animal.

10. The method of claim 8, wherein the administration is parenteral.

11. The method of claim 10, wherein the administration is intramuscular.

12. A method of formulating a vaccine composition, comprising:
rehydrating a mixture of lyophilized antigen, linear chitosan, and a crosslinking agent, and
crosslinking the chitosan upon rehydration,
wherein the antigen is a rattlesnake venom and the method further comprises thermally inactivating the rattlesnake venom prior to lyophilization, wherein the thermally inactivated rattlesnake venom is present in in the composition at a concentration ranging from about 1 to 10 mg/mL.

13. The method of claim 12, further comprising: prior to rehydrating, lyophilizing the antigen with the crosslinking agent; and wherein the rehydrating comprises adding the lyophilized antigen and crosslinking agent to a solution containing the chitosan.

14. The method of claim 12, wherein the inactivating comprises exposing the rattlesnake venom to a temperature of at least 75° C. for a period of time of at least 2 minutes.

15. The method of claim 14, wherein the temperature is at least 85° C. for at least 5 minutes.

* * * * *